United States Patent [19]

Regimand

[11] Patent Number: 5,151,601
[45] Date of Patent: Sep. 29, 1992

[54] NUCLEAR GAUGE WITH COMPENSATION FOR SAMPLE OF INSUFFICIENT NEUTRON MODERATING ACTIVITY

[75] Inventor: Ali Regimand, Raleigh, N.C.

[73] Assignee: Troxler Electronic Laboratories, Inc., Research Triangle Park, N.C.

[21] Appl. No.: 656,959

[22] Filed: Feb. 15, 1991

[51] Int. Cl.[5] .............................................. G01N 23/09
[52] U.S. Cl. ............................ 250/390.04; 250/390.05
[58] Field of Search ..................... 250/390.04, 390.05, 250/390.10, 392

[56] References Cited

U.S. PATENT DOCUMENTS

| | | | |
|---|---|---|---|
| 3,492,479 | 1/1970 | Lowery et al. | 250/390.04 |
| 4,164,655 | 8/1979 | Noma et al. | 250/390.04 |
| 4,499,380 | 2/1985 | Aggour et al. | 250/390.04 |
| 4,864,842 | 9/1989 | Regimand | 250/390.06 |
| 4,874,950 | 10/1989 | Regimand | 250/390.04 |

OTHER PUBLICATIONS

Freeman, Thomas E. et al., Engineering Report—Asphalt Content Determination of Marshall Specimens by The Nuclear Method, Sep. 1985, Department of Civil Engineering, Clemson University.

*Primary Examiner*—Carolyn E. Fields
*Attorney, Agent, or Firm*—Bell, Seltzer, Park & Gibson

[57] ABSTRACT

Method and apparatus for determining the asphalt content of a bituminous paving mix wherein Marshall plug samples of the bituminous paving mix are subjected to a neutron source and the neutrons that are thermalized by hydrogen nuclei present in the Marshall plug sample are detected and counted to provide an indication of the asphalt content of the sample. A neutron moderating substance, such as a polyethylene sample holder having receptacles for closely fitting the Marshall plug samples, is included with the sample pan to increase the number of thermalized neutrons resulting from the interaction of neutrons with hydrogen nuclei present in the sample.

14 Claims, 3 Drawing Sheets

NUCLEAR GAUGE WITH COMPENSATION FOR SAMPLE OF INSUFFICIENT NEUTRON MODERATING ACTIVITY

BACKGROUND OF THE INVENTION

Lowery, et al. U.S. Pat. No. 3,492,479 discloses a portable nuclear gauge that utilizes a fast neutron source and a thermal neutron detector for determining the composition of a bulk material placed in a sample pan. This gauge is particularly useful for measuring the asphalt content of a bituminous paving mix. This type of gauge relies upon the neutron moderating characteristics of hydrogen present in the composition for determining, for example, the amount of asphalt in a paving mix or the amount of moisture in a building material. For these determinations it is known that the amount of asphalt or the amount of moisture can be related to the hydrogen content of the material. The hydrogen content of the material can be determined by subjecting the sample to radiation from a fast neutron source and detecting neutrons that have been slowed or thermalized as a result of interaction with the hydrogen nuclei present in the sample. The number of thermalized neutrons detected and counted over a period of time is utilized in determining the hydrogen content of the sample.

A more recent model of this gauge has been produced by applicant's assignee embodying the principles of the Lowery patent and sold as the "Model 3241 Asphalt Content Gauge" by Troxler Electronic Laboratories, Inc. One such gauge is described in U.S. Pat. No. 4,874,950. This gauge includes a microprocessor to facilitate calibration and computation of the asphalt content of the sample.

A typical procedure for preparing samples for testing involves weighing a sample pan, filling the sample pan carefully, and compacting the samples to a uniform volume and weight. For determining the asphalt content of a bituminous paving mix, this procedure entails filling a sample pan with a loose, well-mixed paving mix and carefully compacting the loose mix so that all the test samples will have the same density.

In the course of manufacturing and applying the bituminous paving mix to form pavement, various measurements and tests of the paving mix are customarily made in addition to measuring asphalt content. Many of these tests and measurements require the use of standardized samples, or sample plugs, which are made according to well-established procedures. One such test that is used to measure the compactability of the mix requires the preparation of standardized samples called Marshall plugs. A known weight of paving mix is placed into a compaction mold and hit a predetermined number of times with a hammer of known weight to form a compacted cylindrical plug, the Marshall plug, of about 4 inches diameter and about 3 inches height, from which compactability is measured.

Since standardized samples, such as Marshall plug samples, are already being prepared by these producers and users, it would be convenient if these same standardized samples could be used in the measurement of asphalt content. By using existing samples and avoiding the need for separately preparing a larger sample, the asphalt content determination could be made more quickly and easily. However, prior attempts to use standardized samples such as Marshall plug samples in the measurement of asphalt content have been unsuccessful. The measurement readings were not of sufficient accuracy and reproducibility to be acceptable. In this regard, several years ago applicant's assignee commissioned a university to investigate how to use Marshall plug samples in the measurement of asphalt content with the Troxler 3241 Asphalt Content Gauge. This study is described in a 1985 engineering report of the Department of Civil Engineering of Clemson University entitled, Asphalt Content Determination of Marshall Specimens by the Nuclear Method. However the test procedure reported in this study was never adopted commercially because it did not provide acceptably accurate and reproducible asphalt content readings.

With the foregoing in mind, it is an object of the present invention to overcome the limitations of the prior practices discussed above and to provide a method and apparatus capable of accurately measuring samples that are already customarily prepared so as to thus avoid the necessity of a separate sample preparation step.

SUMMARY OF THE INVENTION

The present invention is based upon the recognition that the volume of the Marshall plug samples is insufficient to provide an adequate level of thermalized neutrons for accurate and reproducible determination of the asphalt content of the sample. In accordance with the present invention, an auxiliary neutron moderating substance is provided in the neutron gauge along with the hydrogen-containing test sample for increasing the interaction of neutrons in the vicinity of the test sample. The hydrogen content of the test sample is determined from a count of neutrons thermalized by the combined effects of the test sample and the auxiliary neutron moderating substance.

In accordance with one aspect of the present invention, there is provided an apparatus for determining the asphalt content of a bituminous paving mix. The apparatus comprises a neutron gauge having a gauge housing adapted for receiving a sample therein so that the hydrogen-content thereof can be measured. A neutron source is provided in the housing for subjecting the sample to neutrons, and detector means provided in the housing for detecting thermalized neutrons. Means is provided cooperating with said detector means for calculating from the thus detected thermalized neutrons the hydrogen content of the hydrogen-containing sample. An auxiliary neutron moderating substance is provided in the gauge housing in the vicinity of the hydrogen-containing sample for increasing the interaction of neutrons from said source with hydrogen nuclei present in the sample. Preferably, the auxiliary neutron moderating substance comprises a fixed quantity of the neutron moderating substance which is located within the gauge housing in a fixed position in relation to said source and detector means. In one embodiment of the apparatus, the auxiliary neutron moderating substance is a block of polyethylene. More specifically, the auxiliary neutron moderating substance is a polyethylene sample holder that fits into a conventional sample pan and which is provided with receptacles for closely receiving Marshall plug samples of the bituminous paving mix.

In yet another aspect of the present invention, there is provided a process for determining the asphalt content of a bituminous paving mix. The process comprises forming the bituminous paving mix into a plug-shaped sample, positioning the plug-shaped sample in a sample holder having a sample receptacle formed therein of a size and shape adapted to closely receive the plug-shaped sample, and which is formed of a hydrogen-containing substance, subjecting the sample holder with the plug-shaped sample positioned therein to a neutron source, detecting neutrons that have been thermalized by the combined effects of the sample holder and plug-shaped sample, and determining the asphalt content of the plug-shaped sample based upon the thus detected thermalized neutrons.

In one embodiment of the process, the counts of thermalized neutrons, whether for test sample or calibration, are the average of four counts. After taking the first count, the sample is rotated 180° about a vertical axis and a second count is taken. Then the sample is turned over and a third count is taken. The fourth count is taken after the sample has been again rotated 180° about a vertical axis.

In yet another embodiment, background counts are taken prior to calibration and prior to determining the asphalt content of test samples. The difference between these two counts is taken, and the count determined for the combined effects of test sample and neutron moderating substance is adjusted thereby. Asphalt content is determined from the combined count.

BRIEF DESCRIPTION OF THE DRAWINGS

Some of the features and advantages of the invention having been stated, others will become apparent as the description proceeds, and taken in connection with the accompanying drawings, in which.

DETAILED DESCRIPTION OF THE PREFERRED EMBODIMENTS

The present invention will now be described more fully, with reference to the drawings, in connection with a particular type of neutron gauge designed for measuring the asphalt content of bituminous paving mixes. This invention can, however, be used with other types of neutron gauges to measure properties that can be correlated with the hydrogen content of a sample material. For example, the invention can be used to determine the amount of moisture in a building material. It should be understood therefore that the specific embodiments described herein are illustrative of how the present invention may be practiced, and that the invention is not limited to these specific embodiments.

Figure 1:
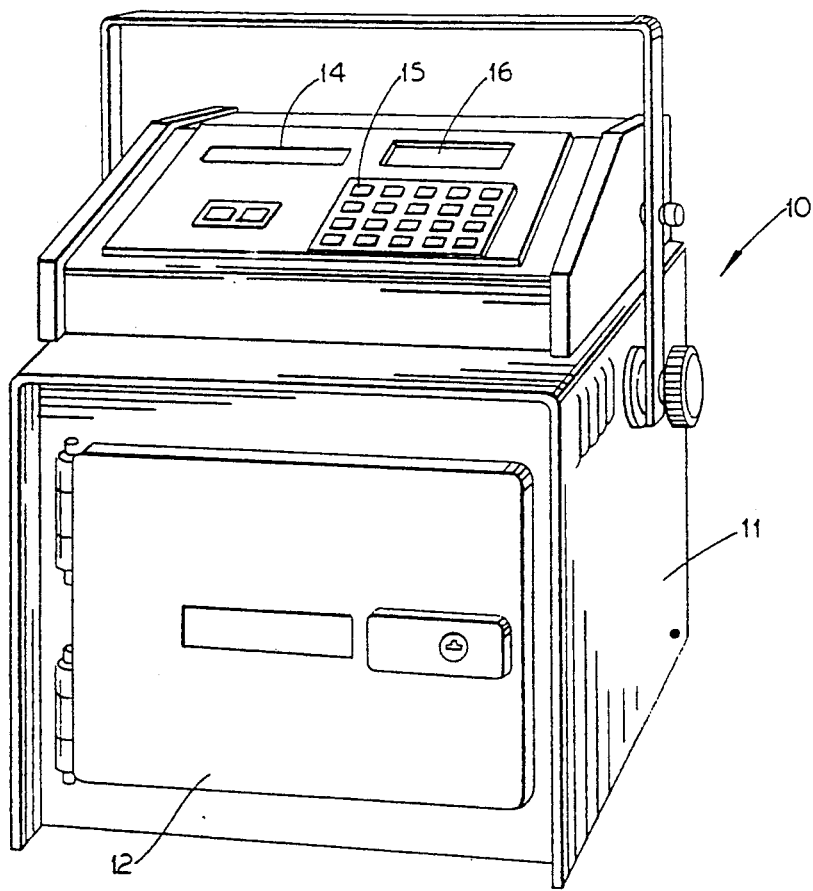
FIG. 1 is a perspective view of a neutron gauge.

A neutron gauge is generally indicated by the number 10 in FIG. 1 and comprises a generally rectangular housing 11 having a door 12 that provides access to a measurement chamber in which sample pans are placed for measurement. A control unit 14 is provided, including a keypad 15 for entry of data and for controlling the functions of the gauge, and a display 16, which may be of any suitable construction, such as a liquid crystal display.

Figure 2:
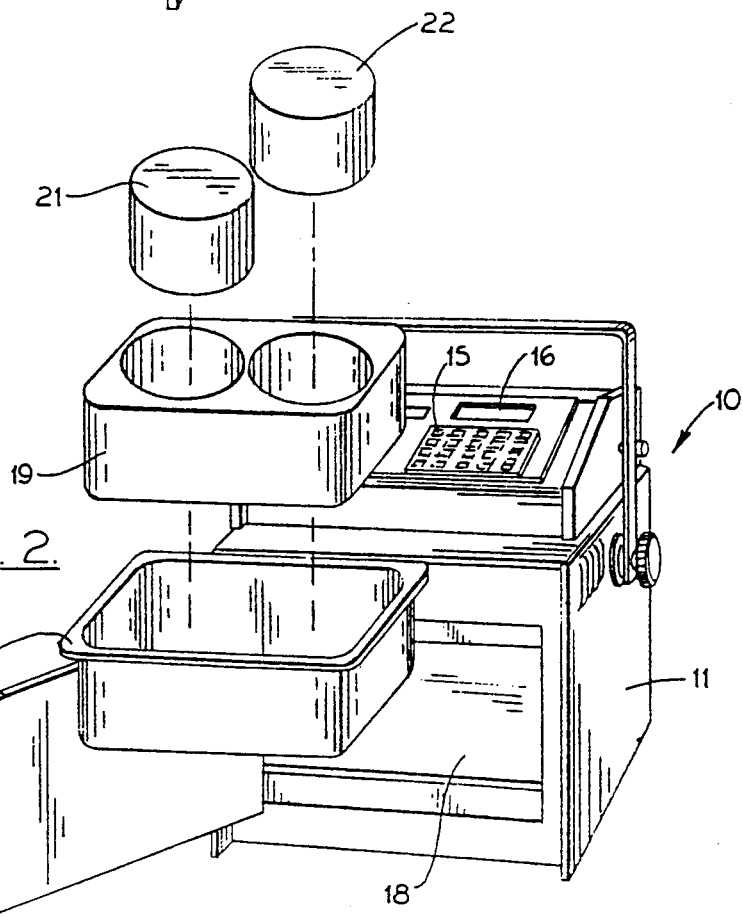
FIG. 2 is an exploded perspective view of the neutron gauge of FIG. 1, a sample tray, a polyethylene insert, and two Marshall plugs, showing their interrelationship with each other.

Referring to FIG. 2, there is shown in exploded view the components of the present invention. A sample pan 17 is sized to fit into the measurement chamber 18 of the neutron gauge. A sample holder 19 is shown disposed above the sample pan and is sized to be closely fitted within the sample pan. Sample holder 19 is formed of a neutron moderating substance. In the illustrated embodiment, for example, the sample holder is formed of a block of polyethylene. Since polyethylene contains a fixed amount of hydrogen in its molecular structure, it effectively serves as a neutron moderating substance. In addition, polyethylene is relatively inert and its hydrophobic property renders it relatively unaffected by changes in ambient moisture. It will be appreciated, however, that other materials may be used as the neutron moderating substance, so long as the material does not chemically react with the sample material, does not absorb or release moisture, and provides neutron moderating activity. For example, a water filled polyethylene or metal sample holder should be suitable. As illustrated, the sample holder 19 has cylindrical holes formed therein which are of a size and shape adapted to closely receive a test sample. Plug-shaped samples 21 and 22 are shown disposed above the sample holder and sample tray. These samples may suitably comprise Marshall or other plugs or core samples formed in a conventional manner in connection with tests for asphalt compactability including core samples from a paved highway.

In the preferred embodiment illustrated herein, the sample holder itself serves as the auxiliary neutron moderating substance. This assures that the auxiliary neutron moderating substance is located in close proximity to the test sample so that the auxiliary neutron moderating substance provides additional interactions to increase the flux, or density, of slow neutrons surrounding and thus interacting with the sample. Accordingly, fewer interactions are required for the sample to thermalize a neutron to a detectable level, and the number of effective interactions to thermalize a neutron is increased. It should be understood, however, that the auxiliary neutron moderating substance could be provided in other configurations and at other locations within the gauge than as illustrated, while still reaping the benefits of this invention.

In order to obtain the most accurate and reproducible results, it is also important that the auxiliary neutron moderating substance be positioned in a fixed or consistent location in relation to the source and detector. Because the auxiliary neutron moderating substance is located in the sample pan and the pan is designed to be received in the same location within the sample-receiving cavity of the gauge housing, this consistent positional relationship is achieved.

Figure 3:
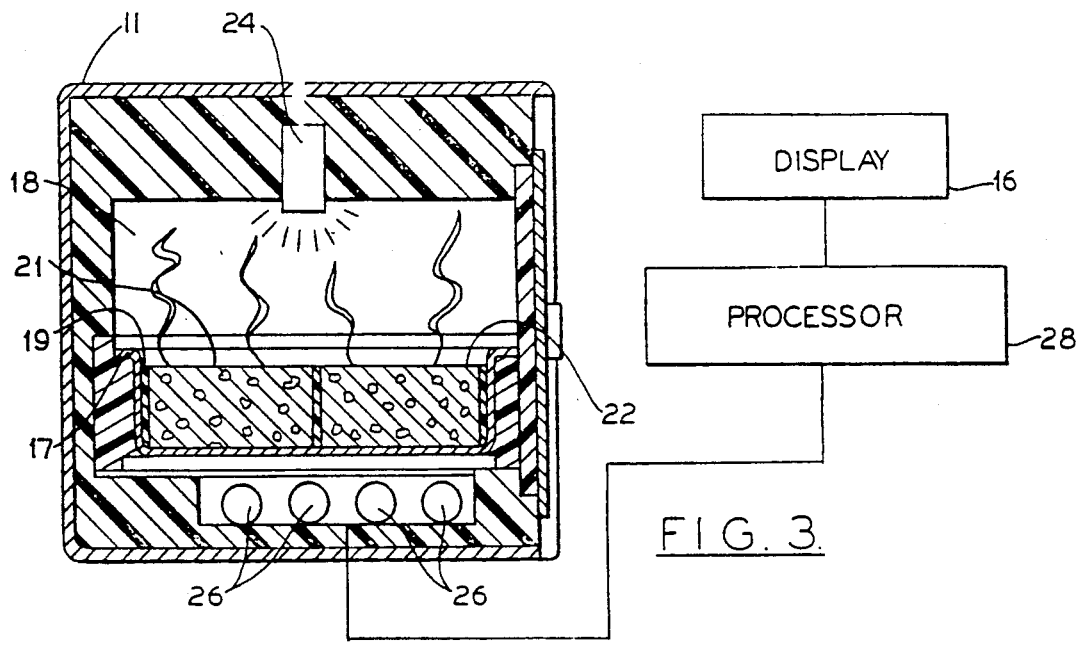
FIG. 3 is a front cross-sectional view of the neutron gauge of FIG. 1 having placed therein a sample tray, polyethylene insert, and two Marshall plugs in accordance with the present invention.

Referring to FIG. 3, measurement chamber 18 receives sample pan 17, sample holder 19, and plug-shaped samples 21 and 22. Located in the upper interior portion of the gauge is a source 24 of fast neutrons. The source 24 may, for example, suitably comprise an Am-241:Be source. In the lower interior portion of the gauge beneath the sample pan are a series of detector tubes 26 for detecting neutrons that have been slowed or thermalized by interaction with hydrogen atoms present in the sample and sample holder. The illustrated detectors 26 are $He^3$ detector tubes, but any suitable thermal neutron detector will suffice. The gauge also includes a processor module 28 for controlling the gauge and counting thermalized neutrons.

To operate the gauge, the plug-shaped samples are placed in the receptacles of the sample holder in the sample pan and inserted into the interior of the gauge. The door is shut and fast neutrons from the source 24 are emitted down through the samples 21 and 22 and sample holder 19 in the sample pan 17. Fast neutrons from the source interact with hydrogen nuclei present in the samples and in the sample holder. Detector 26 detects thermalized neutrons below a specified energy level. The thermalized neutrons are counted for a predetermined period and a count is recorded in the data processor module 28. The processor module 28 then correlates the number of counts to an asphalt content by using a previously established calibration to indicate the result in display 16 for the bituminous paving mix being tested.

The basic procedure for determining the asphalt content of test samples is described with reference to the flow diagram illustrated in FIG. 4. It is first necessary to calibrate the gauge, as shown in steps 30, 32 and 34. plug-shaped samples of bituminous paving mix of known asphalt content are formed as indicated at 30. These samples are then placed in receptacles of a polyethylene sample holder and placed in a neutron gauge, which is then calibrated with respect to the known samples, in accordance with steps 32 and 34.

Figure 4:
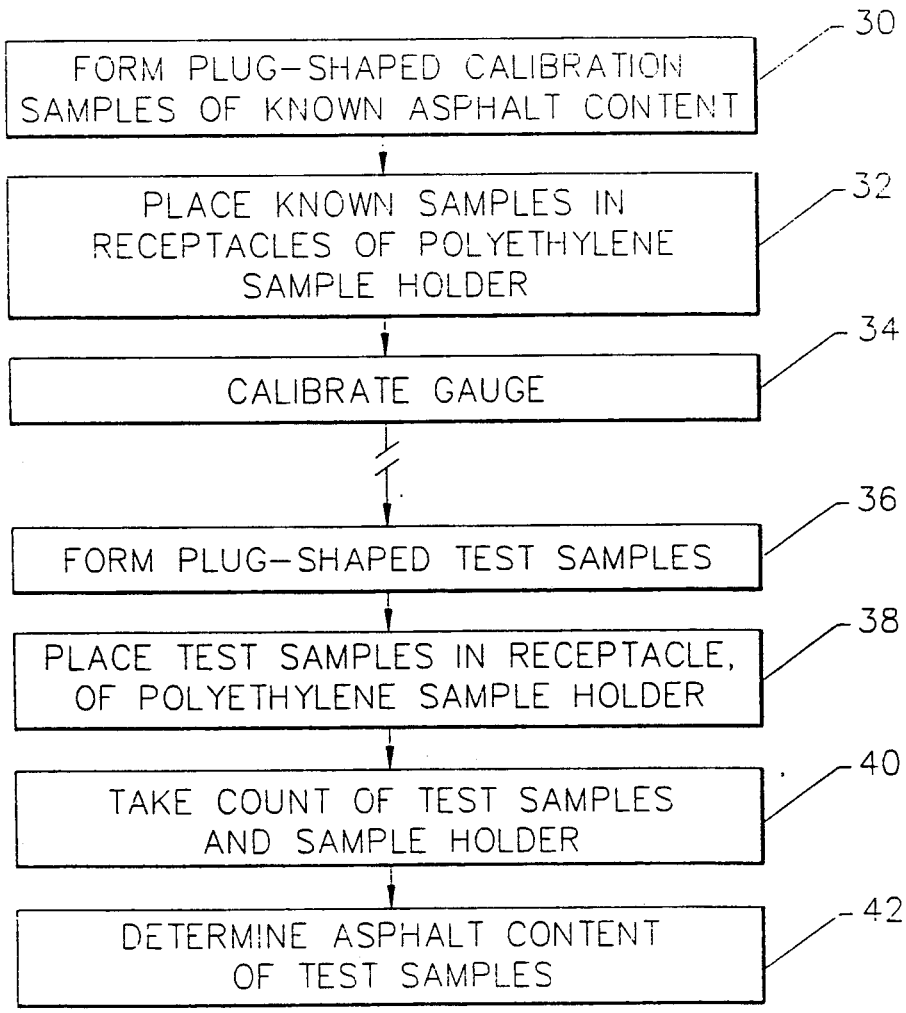
FIG. 4 is a flow chart illustrating the basic procedures followed according to one embodiment of the present invention.

Test samples of unknown asphalt content are formed into plugs following the same procedure as used for forming the samples of known asphalt content, as illustrated in FIG. 4 at 36. As illustrated in steps 38 and 40, these samples are placed in receptacles of the polyethylene sample holder, and counts of the test samples and sample holder are then taken. Finally, in accordance with step 42, the asphalt content of the test samples is determined from the counts of the test samples in accordance with the predetermined calibration.

To calibrate the gauge, a first measurement is made of the background count of thermalized neutrons. This level will change with the location of the gauge, and it is recommended that the background count be determined every day. Changes in the background count from that established when the gauge was calibrated can then be taken into account in calculating the asphalt content of test samples.

Once the background count is determined, measurements of neutron moderating activity are made on each of two or more plug-shaped samples of known asphalt content, each of which has a slightly different asphalt content, for calibration of the apparatus. For example, counts may be taken for three different samples, one having an asphalt content of 4%, one of 5%, and one of 6%. The samples are placed in the receptacles of the polyethylene sample holder, subjected to a source of neutrons, and the thermalized neutrons are detected and counted. The count obtained is from the combination of the sample and sample holder.

When the material to be tested is a bituminous paving mix that has been formed into plug-shaped samples such as Marshall plugs, then it is possible that this sample can have a nonhomogeneous distribution of asphalt and aggregate. In this case, a single count from the sample, whether for calibration or testing, may not provide sufficiently accurate results. Accordingly, it is preferred to obtain several counts for each sample in various positions to ensure accuracy and repeatability of results.

Figure 5:
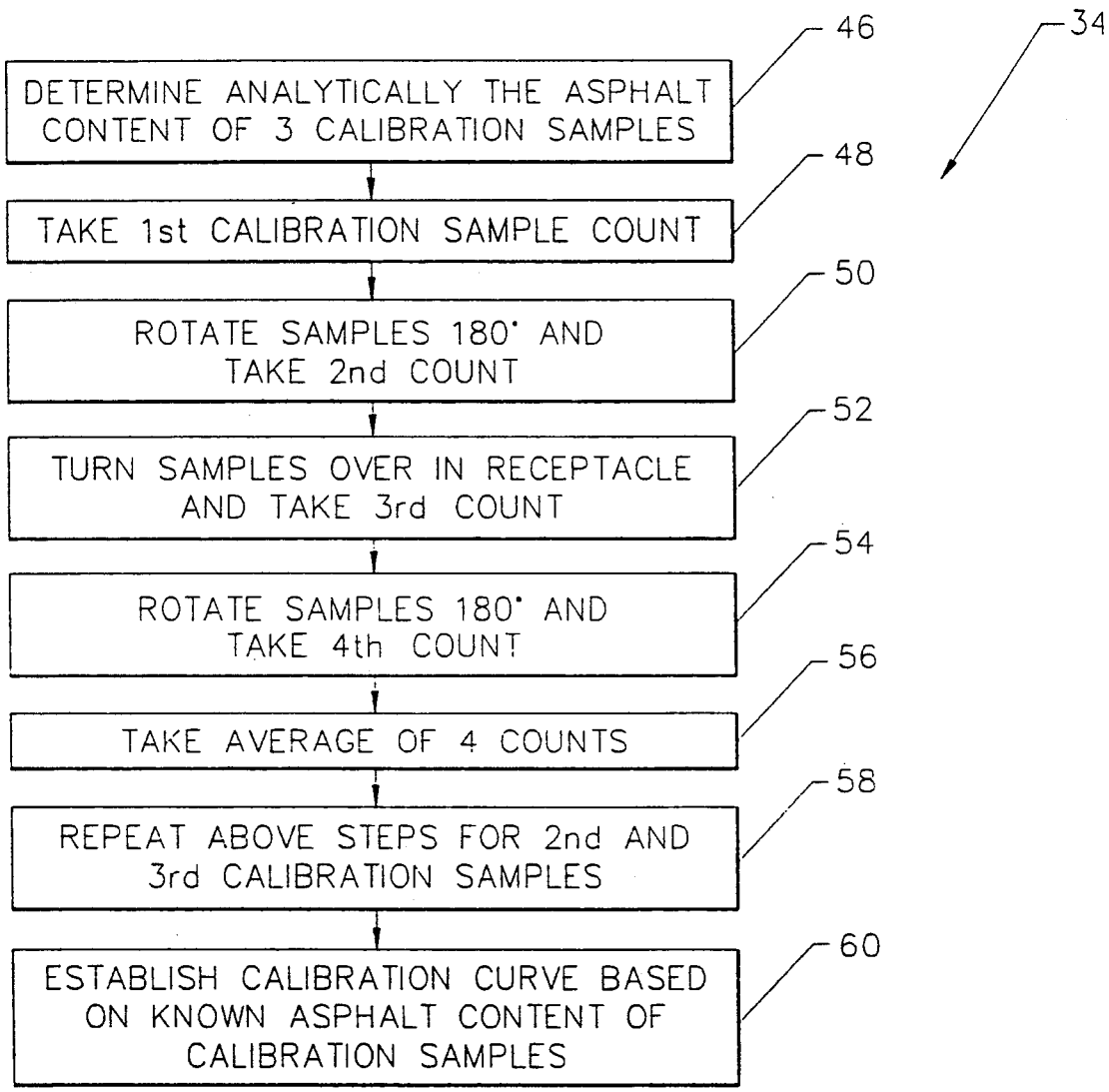
FIG. 5 is a flow chart illustrating detailed procedures for calibrating a neutron gauge in one embodiment of the present invention.

The procedure for calibrating a neutron gauge to determine the asphalt content of bituminous paving mixes from Marshall plug samples is described with reference to FIG. 5. The first step, as illustrated at 46, is to determine analytically the asphalt content of several samples. Generally speaking, at least two samples of different percent asphalt should be analyzed for use in establishing a calibration curve. However, it is preferred to analytically establish the asphalt content of three or more samples. These three samples can be used, for example, to establish the norm and the upper and lower limits for asphalt content for test samples of unknown asphalt content.

After the asphalt content of the known samples has been determined analytically, then, as illustrated at 48, a count is taken of the first known sample. The known sample is rotated 180°, and a second count is taken as illustrated at 50. As illustrated at 52, the plugs should be turned over in the receptacle and a third count taken. As illustrated at 54, the sample holder is again rotated 180° and a fourth count is taken. The unknown test samples should be prepared and measured similarly.

After the four counts of the known samples have been taken in accordance with the standard procedure as illustrated at 48–54, then, as illustrated at 56, the average of the four counts is taken. As illustrated at 58, these steps are repeated for the second and third test samples and then, as illustrated at 60, calibration curve is established based on the known asphalt content of the calibration samples and the average counts obtained for them. The counts obtained for the samples can be fitted to a polynomial or any suitable equation. The parameters for the calibration equation are stored in processor 28, which is illustrated in FIG. 3, and these parameters are thereafter used to determine the asphalt content of unknown test samples. In this manner, the gauge is calibrated to determine the asphalt content of unknown test samples from the combined counts of the test sample and sample holder. The average of four counts taken from an unknown test sample can then be used in the calibration equation to determine the percent asphalt of the sample.

While it is somewhat simpler to calibrate the gauge to determine the property being measured directly from the count resulting from the combination of test sample and neutron moderating substance, one can also calibrate the gauge by first taking the measurement of the hydrogen content of the neutron moderating substance and using this value as the background. This count can then be used to adjust all subsequent counts taken by the gauge. Alternatively, one can also determine the hydrogen content of the neutron moderating substance, generate a correction factor that is a function of the hydrogen content of the substance, and apply that correction factor to the combined measurement of the hydrogen content of the substance and test sample.

That which is claimed is:

1. An apparatus for determining the hydrogen content of a hydrogen-containing material wherein the apparatus subjects a sample of the hydrogen-containing material to neutron radiation from a fast neutron source contained in the apparatus and then detects neutrons that become thermalized by interacting with hydrogen nuclei present in the hydrogen-containing material, the apparatus comprising, in combination:

a gauge housing adapted for receiving a sample therein so that the hydrogen-content thereof can be measured, a neutron source provided in the housing for subjecting the sample to neutrons, detector means provided in the housing for detecting thermalized neutrons, means cooperating with said detector means for calculating from the thus detected thermalized neutrons the hydrogen content of the hydrogen-containing sample, and a sample holder adapted to be positioned within said gauge housing, said sample holder being formed of a hydrogen-containing substance and having at least one receptacle formed therein of a size and shape adapted for closely receiving the hydrogen-containing sample and surrounding said sample with said hydrogen-containing substance, said sample holder thus increasing the interaction of neutrons from said source with hydrogen nuclei present in the sample.

2. An apparatus according to claim 1 wherein said hydrogen-containing substance comprises a block of polyethylene.

3. An apparatus for determining the asphalt content of a bituminous paving mix formed into a plug-shaped sample, said apparatus comprising, in combination:

a gauge housing having a sample receiving cavity therein, a sample holder adapted to be positioned in the sample receiving cavity of said housing, said sample holder being formed of a hydrogen-containing substance, and said sample holder having at least one receptacle formed therein of a size and shape adapted to closely receive a plug-shaped sample of the bituminous paving mix, a neutron source provided in said housing for subjecting a sample holder with a plug-shaped sample positioned therein to neutrons, detector means provided in said housing for detecting thermalized neutrons, and means cooperating with said detector means for calculating from the thus detected thermalized neutrons the asphalt content of the plug-shaped sample of bituminous paving mix.

4. An apparatus according to claim 3 wherein the sample holder is formed of polyethylene.

5. An apparatus according to claim 4 wherein the sample holder has two cylindrical receptacles adapted for receiving plug-shaped samples in the form of cylindrical Marshall plugs.

6. An apparatus for determining the asphalt content of a bituminous paving mix formed into Marshall plugs, said apparatus comprising, in combination:

a gauge housing having a door that provides access to a sample receiving cavity in the gauge housing, a control unit for the gauge housing including a keypad for entry of data and for controlling the functions of the gauge and a display for displaying measurements obtained by the gauge, a metal sample pan sized to closely fit into the sample receiving cavity, a sample holder sized to closely fit into the sample pan and having two cylindrical sample receptacles formed therein of a size and shape to closely receive the Marshall plug samples, the sample holder being formed of polyethylene, an Am-241:Be neutron source provided in said housing for subjecting the sample holder and Marshall plug samples positioned therein to neutrons, $He^3$ detector tubes provided in said housing for detecting neutrons thermalized by the neutron moderating characteristics of the polyethylene sample holder and Marshall plug samples, a processor cooperating with the detector tubes for calculating from the detected thermalized neutrons the asphalt content of the Marshall plug samples of bituminous paving mix.

7. An improvement in the method of determining the hydrogen content of a hydrogen-containing material wherein a sample of the material is subjected to a fast neutron source and a measurement is made of neutrons that are thermalized by hydrogen nuclei present in the sample, said improvement comprising providing a sample holder formed of a hydrogen-containing substance and having at lest one receptacle formed therein for closely receiving a hydrogen-containing sample and surrounding the sample with the hydrogen-containing substance for increasing the interaction of neutrons from the source with hydrogen nuclei present in the sample, locating the sample holder within the housing of the gauge, and determining the hydrogen content of the sample based upon a count of neutrons thermalized by the combined effects of the sample and the hydrogen-containing substance.

8. A method for determining the asphalt content of a bituminous paving mix, comprising:

forming the bituminous paving mix into a plug-shaped sample, positioning the plug-shaped sample in a sample holder having a sample receptacle formed therein of a size and shape adapted to closely receive the plug-shaped sample, and which is formed of a hydrogen-containing substance, subjecting the sample holder with the plug-shaped sample positioned therein to a neutron source, detecting neutrons that have been thermalized by the combined effects of the sample holder and plug-shaped sample, and determining the asphalt content of the plug-shaped sample based upon the thus detected thermalized neutrons.

9. A method according to claim 8 wherein the step of positioning the plug-shaped sample in a sample holder comprises positioning the plug-shaped sample in a block of polyethylene having a hole formed therein of a size and shape adapted to closely receive the plug-shaped sample.

10. A method for determining the asphalt content of a bituminous paving mix, the method comprising:

a) providing a neutron gauge having a sample pan, b) providing a polyethylene sample holder in combination with the sample pan, the polyethylene sample holder having at least one receptacle formed therein adapted to receive plug-shaped samples of the bituminous paving mix, c) calibrating the neutron gauge to determine the asphalt content of the bituminous paving mix from a count of thermalized neutrons resulting from the combined effects of the plug-shaped samples and polyethylene sample holder, d) placing a plug-shaped sample in each receptacle of the sample holder in the neutron gauge, e) obtaining a count of neutrons thermalized by the combined effects of the plug-shaped samples and polyethylene sample holder, and f) determining the asphalt content of the bituminous paving mix from the thus obtained count of thermalized neutrons.

11. The method according to claim 10 wherein the step (c) of calibrating the neutron gauge comprises:
   a) placing a first plug-shaped sample of predetermined asphalt content in each receptacle of the polyethylene sample holder in the sample pan in the neutron gauge,
   b) subjecting the plug-shaped samples and polyethylene sample holder to a source of fast neutrons in the gauge,
   c) detecting neutrons thermalized by hydrogen present in the samples and sample holder,
   d) counting the detected neutrons and storing this count,
   e) rotating the samples 180° about a vertical axis to a second position and repeating steps (b-d),
   f) rotating the samples 180° about a horizontal axis to a third position and repeating steps (b-d)
   g) rotating the samples 180° about a vertical axis to a fourth position and repeating steps (b-d)
   h) calculating the average of the four counts of the plug-shaped samples and polyethylene sample holder determined in steps (b-g) to determine an average count,
   i) repeating steps (a) through (h) for one or more remaining plug-shaped samples having predetermined asphalt contents different from the first such plug-shaped sample and different from each other, and
   j) establishing a calibration curve based upon the average count calculated according to step (h) of the plug-shaped samples of predetermined asphalt content and the predetermined asphalt content of each sample.

12. The method according to claim 10 wherein the step (e) of obtaining a count of neutrons thermalized by the combined effects of the plug-shaped samples and polyethylene sample holder comprises:
   a) subjecting the plug-shaped samples and polyethylene sample holder to a source of fast neutrons in the gauge,
   b) detecting thermalized neutrons,
   c) counting the detected neutrons and storing this count,
   d) rotating the samples 180° about a vertical axis to a second position and repeating steps (a-c),
   e) rotating the plug-shaped samples 180° about a horizontal axis to a third position and repeating steps (a-c),
   f) rotating the samples 180° about a vertical axis to a fourth position and repeating steps (a-c), and
   g) calculating the average of the four counts of the plug-shaped samples and polyethylene sample holder determined in steps (a-f) to determine an average count.

13. The method according to claim 10 wherein the method includes the additional steps of taking a background count prior to calibrating the neutron gauge according to step (c) and storing this count, taking another background count prior to obtaining a count according to step (e), calculating the difference between the two background counts, adjusting the count obtained according to step (e) by the difference in background counts, and then determining the asphalt content of the bituminous paving mix according to step (f) from the adjusted count.

14. An improvement in the method of determining the hydrogen content of a bituminous paving mix wherein a sample of the paving mix is subjected to a fast neutron source and a measurement is made of neutrons that are thermalized by hydrogen nuclei present in the sample, said improvement comprising forming the bituminous paving mix into at least one plug-shaped sample, positioning the plug-shaped sample in a sample holder that is formed of a hydrogen-containing substance and has at least one receptacle formed therein for closely receiving the plug-shaped sample for increasing the interaction of neutrons from the source with hydrogen nuclei present in the sample, locating the sample holder within the housing of the gauge, and determining the hydrogen content of the sample based upon a count of neutrons thermalized by the combined effects of the sample and the hydrogen-containing substance.

* * * * *